US012682897B2

(12) United States Patent
Mayer et al.

(10) Patent No.: US 12,682,897 B2
(45) Date of Patent: Jul. 14, 2026

(54) MOTOR VEHICLE AND METHOD FOR SUMMARIZING A CONVERSATION IN A MOTOR VEHICLE

(71) Applicant: CARIAD SE, Wolfsburg (DE)

(72) Inventors: Stefan Mayer, Gaimersheim (DE);
Sebastian Hanrieder, Untermaxfeld
(DE); Tobias Schleicher, Wettstetten
(DE); Markus Mueller, Hohenwart
(DE); Mareike Grund,
Fürstenfeldbruck (DE); **Benjamin
Poppinga**, Wettstetten (DE)

(73) Assignee: CARIAD SE, Wolfsburg (DE)

( * ) Notice: Subject to any disclaimer, the term of this
patent is extended or adjusted under 35
U.S.C. 154(b) by 109 days.

(21) Appl. No.: 18/478,818

(22) Filed: Sep. 29, 2023

(65) Prior Publication Data

US 2024/0112677 A1     Apr. 4, 2024

(30) Foreign Application Priority Data

Oct. 4, 2022     (DE) .......................... 102022125547.6

(51) Int. Cl.
*G10L 15/22*          (2006.01)
*A61B 5/00*          (2006.01)
             (Continued)

(52) U.S. Cl.
CPC .............. *G10L 15/22* (2013.01); *A61B 5/024*
(2013.01); *A61B 5/165* (2013.01); *A61B 5/18*
(2013.01);
             (Continued)

(58) Field of Classification Search
CPC ........ B60W 40/08; B60W 9/02; B60W 50/14;
G10L 15/22; G10L 15/1815; G10L 15/18;
             (Continued)

(56) References Cited

U.S. PATENT DOCUMENTS

2004/0063472 A1* 4/2004 Shimizu .............. H04M 1/6091
                                                                455/569.1
2013/0163776 A1* 6/2013 Yamkovoy ....... G10K 11/17885
                                                                381/72
             (Continued)

FOREIGN PATENT DOCUMENTS

CN         106491104 A * 3/2017 .......... A61B 5/7455
DE     112012006617 T5     4/2015
             (Continued)

OTHER PUBLICATIONS

Nanxiang Li, et al. "Detecting Drivers' Mirror-Checking Actions
and Its Application to Maneuver and Secondary Task Recognition",
IEEE Transactions on Intelligent Transportation Systems, vol. 17,
No. 4, (Year: Apr. 2016).*

*Primary Examiner* — Leshui Zhang
(74) *Attorney, Agent, or Firm* — Seed Intellectual
Property Law Group LLP

(57)          ABSTRACT

The disclosure relates to a motor vehicle and a method for
summarizing a conversation in a motor vehicle. The method
involves determining by a vehicle sensor device whether a
challenging driving task is present; if the challenging driving
task is present, masking a conversation in the motor vehicle
for a driver by generating counter noise; recording the
conversation in the motor vehicle by at least one vehicle
microphone; summarizing the conversation by artificial
intelligence; outputting a summary of the conversation to the
driver after determining that the challenging driving task is
no longer present; and deactivating the counter noise after
the outputting the summary of the conversation.

11 Claims, 2 Drawing Sheets

(51) Int. Cl.

| | |
|---|---|
| *A61B 5/024* | (2006.01) |
| *A61B 5/16* | (2006.01) |
| *A61B 5/18* | (2006.01) |
| *G06N 3/0455* | (2023.01) |
| *G06V 20/58* | (2022.01) |
| *G06V 20/59* | (2022.01) |
| *G10K 11/175* | (2006.01) |
| *G10K 11/178* | (2006.01) |
| *G10L 15/18* | (2013.01) |
| *G10L 25/63* | (2013.01) |

(52) U.S. Cl.
CPC ......... *A61B 5/6893* (2013.01); *G06N 3/0455* (2023.01); *G06V 20/58* (2022.01); *G06V 20/597* (2022.01); *G10K 11/1754* (2020.05); *G10K 11/17823* (2018.01); *G10K 11/17873* (2018.01); *G10L 15/1815* (2013.01); *G10L 25/63* (2013.01); *A61B 2503/22* (2013.01); *G10K 2210/1282* (2013.01); *G10K 2210/3027* (2013.01); *G10K 2210/3044* (2013.01)

(58) Field of Classification Search
CPC ..... G10L 15/24; G10L 19/012; G10L 19/018; G10L 99/00; A61B 5/18; A61B 5/024; A61B 5/165; A61B 5/16; A61B 5/6893; A61B 5/00; B60R 16/0373; B60K 35/10; B60K 35/00; G06V 20/58; G06V 20/597; G06V 20/59; G06N 3/0455; H04M 1/6075; H04M 1/6083; H04M 1/6091; H04M 2250/74; H04M 1/2535; H04M 1/6033; H04M 1/605; H04M 1/6066; H04M 1/6058; H04M 2250/12; H04M 3/533; H04M 1/72433; H04M 1/724
USPC ....... 704/257; 381/302, 71.4, 86, 17.1, 71.8, 381/71.9, 71.11
See application file for complete search history.

(56) References Cited

U.S. PATENT DOCUMENTS

| | | | | |
|---|---|---|---|---|
| 2013/0321171 | A1* | 12/2013 | Tzirkel-Hancock ..... | A61B 5/18 340/905 |
| 2015/0006167 | A1* | 1/2015 | Kato ................. | G01C 21/3608 704/231 |
| 2015/0006278 | A1* | 1/2015 | Di Censo ............ | G06V 20/597 705/14.43 |
| 2015/0137998 | A1* | 5/2015 | Marti ...................... | H04K 3/45 340/901 |
| 2017/0080856 | A1* | 3/2017 | Enomoto ................ | B60Q 9/00 |
| 2018/0204572 | A1* | 7/2018 | Manabe ................. | G10L 13/00 |
| 2020/0219493 | A1* | 7/2020 | Li ........................... | G10L 15/22 |

FOREIGN PATENT DOCUMENTS

| | | | | |
|---|---|---|---|---|
| DE | 102017213249 A1 | 2/2019 | | |
| JP | 2007264436 A | * 10/2007 | ............ | H04K 3/825 |

* cited by examiner

MOTOR VEHICLE AND METHOD FOR SUMMARIZING A CONVERSATION IN A MOTOR VEHICLE

BACKGROUND

Technical Field

The disclosure relates to a method for summarizing a conversation in a motor vehicle as well as a motor vehicle having a system designed to summarize a conversation.

Description of the Related Art

During an automobile trip with multiple passengers, conversations often occur among persons in the vehicle. If the driver of the vehicle is also involved in the conversation, this may represent a not insignificant potential for distraction, especially in a challenging driving situation. In such a situation, the driver must block out the conversation in order to concentrate on the driving task. Depending on the length and content of what was said in the meantime, it may be difficult for him to be again included in the conversation afterwards.

From DE 11 2012 006 617 T5 there is known an onboard information device mounted in the vehicle in order to provide information to assist a passenger. The onboard information device contains a voice detection unit, which continuously detects and records a voice uttered by the passenger while the onboard information device is working. Furthermore, the onboard information device contains a voice detection unit, which recognizes the speech contents of the voice detected by the voice detection unit, a vehicle state detector, which detects the vehicle state, including the state of the environment in the vehicle, an output controller, which generates display data or voice data from the speech contents recognized by the voice detection unit according to the vehicle state detected by the vehicle state detector and controls the output of the display data or voice data, and an output unit which puts out the display data or voice data generated by the output controller.

From DE 10 2017 213 249 A1 there is known a method for generating an auditory message in the interior of a vehicle. The method involves the detecting of a parameter of an acoustic content by a sensor in the interior of the vehicle, and the generating of an auditory message depending on the detected parameter of the acoustic content by a computing unit of the vehicle.

Embodiments of the disclosure improve safety and communication in a vehicle.

BRIEF SUMMARY

The disclosure is based on the idea of automatically masking for the driver a conversation carried on by the passengers in the vehicle during a trip with multiple passengers upon occurrence of a challenging driving task. After the driver has completed the task, an AI-generated summary of what was said in the vehicle in the meantime is read out to him.

The automated masking of the conversation for him is then terminated and he can then once more take part in the conversation.

The disclosure provides a method for summarizing a conversation in a motor vehicle. Preferably there are several persons present in the motor vehicle, communicating with each other. The method involves the steps of determining by a vehicle sensor device whether a challenging driving task is present, masking of a conversation in the motor vehicle for the driver by generating counter noise if the challenging driving task is present, recording of the conversation in the motor vehicle by at least one vehicle microphone, and evaluating and summarizing of the recorded conversation by artificial intelligence. Furthermore, the method involves the putting out of the summarized conversation to the driver once it is determined that the challenging driving task is no longer present, and the deactivating of the counter noise after the output of the summarized conversation.

In other words, at first a vehicle sensor device can examine whether a challenging driving task is recognized or is imminent. A challenging driving task is a driving maneuver requiring heightened attention from the driver of the motor vehicle. For this, a vehicle sensor device, which may comprise multiple vehicle sensors, can detect the environment of the motor vehicle and/or parameters of the driver in the interior of the motor vehicle and ascertain, for example, through an artificial intelligence, whether the challenging driving task is present or not. In particular, an outside camera can detect driving maneuvers of other vehicles and/or weather conditions requiring a heightened concentration when driving the motor vehicle. Also, upcoming traffic infrastructures or traffic situations, such as multiple-lane intersections, off ramps, and/or increased traffic, can display a challenging driving task, for example, from a navigation database. Alternatively or in addition, the degree of attention of the driver can be analyzed, for example, from a view direction analysis and/or pulse sensors, which determine the mental workload of the driver and thus allow an inference of a challenging driving task.

If the challenging driving task is recognized, a conversation taking place between multiple vehicle passengers in the motor vehicle can be masked for the driver, preferably by generating a counter noise at a driver position. The counter noise can reduce and preferably cancel out the sound waves of the conversation traveling in the direction of the driver position. For this, at least one loudspeaker can be arranged around the driver position, which puts out a corresponding counter noise signal to cancel out the sound signal of other persons in the interior, which is determined, for example, by way of corresponding microphones. By counter noise or anti-noise is meant an active noise suppression in which sound is canceled by destructive interference. The counter noise has an opposite polarity to the sound signal coming, for example, from the conversation in the interior. Besides the loudspeakers, headphones worn by the driver can also generate counter noise for the masking of the conversation. The conversation in the interior can also involve, for example, a telephone call through a telephone device of the motor vehicle, in which case the masking of the conversation can be a deactivating of the telephone call for the driver or for a driver position by deactivating the loudspeakers associated with the driver.

While the conversation is being masked for the driver, the conversation of the other vehicle passengers can be recorded by at least one vehicle microphone. The recorded conversation can then be analyzed by an artificial intelligence to determine the conversation contents and/or topic areas. Arguments set forth and/or conversation positions can also be ascertained by the artificial intelligence. For example, the artificial intelligence can be taught to recognize speech, and the artificial intelligence can ascertain key words in order to determine the content of the conversation. By an artificial intelligence or an algorithm for artificial intelligence is meant a program which can process problems on its own, having been taught with teaching data. Thus, the artificial intelligence can recognize patterns, for example, in order to evaluate the conversations, and the evaluated conversations can then be summarized by the artificial intelligence. By a summarizing is meant a shortened version of the conversation, especially one with the most important conversation contents. The artificial intelligence can be, for example, a program specially designed for this, such as GPT-3 (Generative Pre-trained Transformer 3).

After the recorded conversation has been evaluated and summarized, it can be output to the driver, especially after having established that the challenging driving task is no longer present. The output can be a reading aloud of the summary and an output through one or more loudspeakers for the driver. Thus, for example, individual topic areas of the conversation with respective conversation positions of the vehicle passengers can be output for the driver. Once the summarized conversation has been output, the counter noise can finally be deactivated, so that the driver, who no longer needs to concentrate on the challenging driving task, can once again take part in the conversation.

The disclosure affords the benefit of increasing the safety during the operation of the motor vehicle, since the driver is no longer distracted by a conversation in the vehicle during challenging driving tasks. Moreover, the driver can afterwards join the conversation once more, since he is aware of the current conversation content thanks to the summarizing of the conversation, which improves the communication in the motor vehicle.

Embodiments which yield further benefits also belong to the disclosure.

One embodiment proposes that data from at least one vehicle exterior camera and/or navigation system data are examined by an artificial intelligence or the artificial intelligence for the presence of a given driving task criterion in order to determine the challenging driving task. That is, the vehicle sensor device can comprise at least one vehicle exterior camera, which can recognize, for example, driving maneuvers of other vehicles, especially a braking and/or a lane change, which may serve, for example, as a given driving task criterion to indicate the presence of the challenging driving task. It is also possible to determine weather data in the vehicle environment, for example, through the vehicle exterior camera and/or additional weather sensors, and the driving task criterion for indication of the challenging driving task can be, for example, poor visibility, especially rain and/or snow, and wind. Alternatively or in addition, navigation system data can also be evaluated by an artificial intelligence or the artificial intelligence, for example, as to whether a multiple-lane intersection, an off ramp, or increased traffic, especially a traffic jam, is upcoming. In other words, the given driving task criterion which is examined by the artificial intelligence is thus an existing or an upcoming traffic situation for which the driver needs heightened attention. This embodiment affords the benefit that the vehicle sensor device can automatically establish whether a challenging driving task is present.

A further embodiment proposes that a stress value of the driver is determined by one or more vehicle interior sensors in order to determine the challenging driving task, the challenging driving task being present if the stress value is found above a stress threshold value. In other words, the vehicle sensor device can comprise vehicle interior sensors, especially a vehicle interior camera and/or a pulse sensor. These can ascertain a mental workload for the driver in the form of a stress value, and the challenging driving task will be ascertained if the stress value is found above a stress threshold value. Thus, the stress value can be determined from a faster pulse of the driver and/or a state of tension, which can be recognized, for example, by way of the vehicle interior camera. Preferably, the stress value can be determined by the artificial Intelligence or by another artificial intelligence which has been taught, with the aid of teaching data from drivers in stress situations, especially their gestures, facial expressions, bodily tension and view direction analysis, to determine the stress value. This embodiment affords the benefit that an inference of the challenging driving task is possible with the aid of the behavior of the driver.

A further embodiment proposes that the position in the motor vehicle where conversation contents are coming from is determined by one or more vehicle interior sensors, and for the summarizing of the recorded conversation the respective conversation contents of vehicle passengers are coordinated with the respective positions in the motor vehicle and/or wherein the counter noise is calculated in dependence on the ascertained position in the motor vehicle. In other words, the person or the position in the motor vehicle where conversation contents are coming from is determined by vehicle interior sensors. The vehicle interior sensors can be, for example, a vehicle interior camera and/or microphones and/or seat occupancy sensors. Thus, it is possible to ascertain which position or which seat in the motor vehicle is occupied and precisely who is speaking. Thus, on the one hand, the conversation contents can be associated with a particular position or a particular vehicle passenger. This means that the artificial intelligence can then associate conversation contents or arguments with a vehicle passenger for the summarizing, in order to put this out finally during the summarizing of the conversation. On the other hand, the ascertained position from which the conversation contents are coming can be used to compute the counter noise for the driver. Especially favorably, a microphone array can be used for this, making possible a sound triangulation and thus the direction and loudness from which a sound signal reaches the driver position. In turn, the counter noise can be computed from this, in order to generate the destructive interference for the sound signal.

Preferably, it is provided that a respective vehicle passenger is examined by one or more vehicle interior sensors to determine whether a user profile is present for the vehicle passenger, and for the summarizing of the recorded conversation the conversation contents are coordinated with user profile data of the respective user profile. In other words, a recognition of vehicle passengers can be done by vehicle interior sensors. For example, a vehicle interior camera can carry out a facial recognition in order to recognize a vehicle passenger and load a given user profile for this vehicle passenger. Other recognition methods can also be used for this, for example, the vehicle interior sensors may comprise microphones, and a vehicle passenger can be determined through a voice recognition. Moreover, user profiles of respective vehicle passengers can be ascertained by a coupling of mobile terminal devices or a manual input in a vehicle system. If such a user profile exists for a vehicle passenger, the artificial intelligence can coordinate each time the conversation contents output with the vehicle passengers during the summarizing of the conversation, making use of user profile data of the particular user profile. The user profile data may include, in particular, the name of the particular vehicle passenger, in which case the artificial intelligence during the summarizing will provide the conversation contents or arguments with the name of the person who enunciated the arguments. Thus, for example, a summarizing with the coordination of user profile data, especially during debates with strongly opposing positions, may be summarized for example, by the artificial intelligence as follows: "Johannes is arguing for a stock purchase, while Gustav is against it." If the identity of a person cannot be determined, for example, because no user profile exists for that person, the artificial intelligence can alternatively output the position of the person in the motor vehicle with the respective conversation argument, for example: "The person in the middle of the rear seat approves of a stock purchase." In this way, the summarizing of the conversation can be more intuitive and thus better comprehended.

A further embodiment proposes that an emotional state of a respective vehicle passenger during the conversation is determined by one or more vehicle interior sensors, and the summarizing of the conversation includes the ascertained emotional state of the respective vehicle passenger. Thus, vehicle interior sensors can ascertain gestures, facial expressions, the conversation loudness and/or a pulse rate in order to infer from this the emotional state of a vehicle passenger. Thus, for example, laughing or crying can be recognized in order to infer joy or sorrow. Preferably, irony and/or sarcasm can also be ascertained as an emotional state in order to output during the summarizing the emotional state in which a conversation content was uttered. The emotional state can be ascertained by the artificial intelligence or another artificial intelligence which can evaluate the data of the vehicle interior sensors and recognize the corresponding emotional state. Especially preferably, key sentences can also be recognized during the summarizing, such as sentences which were uttered during a high emotional state, and the key sentences can be output during the summarizing as a literal quotation.

A further embodiment proposes that the artificial Intelligence recognizes various topic areas of conversation and summarizes them, and the output of the summarizing of the conversation is done only for the topic areas corresponding to a user preference. In other words, the artificial intelligence can generate multiple topics with respective summaries, while only the topic areas corresponding to a user preference will be output during the summarizing. For example, the artificial intelligence can ascertain a topic area from key words and associate this with spoken conversation contents for the summarizing of the topic areas. The user preference of the vehicle passenger, especially that of the driver, can be specified, for example, from a user profile whereby a user can predetermine which topic areas are of interest to him and which are not. Alternatively, the summarized topic areas can also be presented prior to the summarizing, and the user preference can then be done with the aid of a selection of the topic areas. For example, multiple topic areas can be presented on a display device, especially a head-up display, and the driver can then select through a touch input and/or a voice command input the topic areas which should be read aloud for the summarizing. This embodiment affords the benefit that time can be saved during the putting out of the summarizing, since only those topic areas will be output which are of interest and/or importance to the driver.

In one advantageous embodiment it is provided that a state of distraction of a respective vehicle passenger is additionally determined, and the conversation is masked and summarized for the vehicle passenger whose state of distraction corresponds to a given distraction criterion. In other words, the method can be provided not only for the driver, but also for any given vehicle passenger. The state of distraction of the particular vehicle passenger can be ascertained, preferably with vehicle interior sensors, which measure a distraction or a state of attention of the vehicle passenger.

The distraction criterion for which the conversation will be masked and summarized can be present, for example, when the vehicle passenger receives a call and/or if it is determined that the vehicle passenger is reading or writing a text. If such is the case, the further conversation can be masked accordingly by way of counter noise and the artificial intelligence can create a summary from the recorded conversation, which can be output once the state of distraction of the vehicle passenger is over. This affords the benefit that the communication in the motor vehicle can be improved, since other vehicle passengers can also follow the course of a conversation in event of a distraction.

In another advantageous embodiment it is provided that the conversation is additionally masked for a vehicle passenger in dependence on a user preference, especially with the aid of given conversation contents and/or conversation intensities. This means that a user preference can be memorized, for example, in a user profile as to which conversation contents and/or conversation intensities should be masked for a vehicle passenger. Conversation contents in this case may be topics of no interest to a vehicle passenger given the user preference.

Alternatively or in addition, conversation intensities may also be present by which the conversation in the motor vehicle will be masked. Conversation intensities may be the loudness and/or an emotional course of the conversation, for example, during a conflict. The user preferences of a vehicle passenger may also preferably depend on the time of day and/or the emotional state of the user, which means that the user preference can change in the course of the day, which is preferably stated in a user profile, and/or certain conversation contents and/or conversation intensities can be masked for a user with the aid of a measurement of the emotional state of the user. Also, for example, conversation contents of conversations can be masked by an active command of a vehicle passenger.

A further aspect of the disclosure relates to a motor vehicle having a system for summarizing a conversation, wherein the system is adapted to carry out a method according to one of the preceding embodiments. The system can preferably comprise a vehicle sensor device, one or more loudspeakers, at least one vehicle microphone and a computing device on which an artificial intelligence is operated.

The vehicle sensor device can be adapted to determine whether a challenging driving task is present, the loudspeakers can be adapted to masking a conversation in the motor vehicle for a driver position by generating counter noise if the challenging driving task is present, the at least one vehicle microphone can be adapted to record the conversation in the motor vehicle, and the computing device can be adapted to evaluate and summarize the recorded conversation by an artificial intelligence and to actuate the loudspeakers to output the summarized conversation for the driver after the challenging driving task is no longer present. Finally, the computing device after putting out the summarized conversation can control the loudspeakers to deactivate the counter noise. The same benefits and variation possibilities will obtain here as for the method.

For application cases or situations which may arise during the method and which are not explicitly described here, it can be provided that an error message and/or a request to enter a user feedback will be output according to the method, and/or a standard setting and/or a predetermined initial state will be established.

The disclosure also includes the computing device for the motor vehicle. The computing device can comprise a data processing device or a processor device which is adapted to carrying out one embodiment of the method according to the disclosure. Especially preferably, the computing device can comprise one or more graphic processors (GPU), which are optimized for the operation of the artificial intelligence. For this, the processor device can comprise at least one microprocessor and/or at least one microcontroller and/or at least one FPGA (Field Programmable Gate Array) and/or at least one DSP (Digital Signal Processor). Furthermore, the processor device can comprise program code which is adapted to carrying out the embodiment of the method according to the disclosure when executed by the processor device. The program code can be stored in a data storage of the processor device. The processor circuit of the processor device can comprise, e.g., at least one circuit board and/or at least one SoC (System on Chip).

The disclosure also includes modifications of the motor vehicle according to the disclosure having features as were already described in connection with the modifications of the method according to the disclosure, and vice versa. For this reason, the corresponding modifications of the motor vehicle according to the disclosure will not be described here once more.

The motor vehicle according to the disclosure is preferably designed as an automobile, especially a passenger car or a truck, or as a personal bus.

As a further solution, the disclosure also encompasses a computer-readable storage medium, containing program code which, when executed by a processor circuit of a computer or a cluster of computers, causes them to carry out an embodiment of the method according to the disclosure. The storage medium can be provided, at least partly for example, as a nonvolatile data storage (such as a flash memory and/or as a SSD—solid state drive) and/or at least partially as a volatile data storage (such as a RAM—random access memory). The storage medium can be located in the processor circuit in its data storage. But the storage medium can also be operated, for example, as a so-called appstore server in the Internet. A processor circuit with at least one microprocessor can be provided by the computer or the computer cluster. The program code can be provided as binary code or Assembler and/or as source code of a programming language (such as C) and/or as program script (such as Python).

The disclosure also encompasses the combinations of the features of the described embodiments. Thus, the disclosure also encompasses realizations having a combination of the features of several of the described embodiments, as long as the embodiments were not described as being mutually exclusive.

BRIEF DESCRIPTION OF THE SEVERAL VIEWS OF THE DRAWINGS

In the following, exemplary embodiments of the disclosure are described.

DETAILED DESCRIPTION

The following explained exemplary embodiments are preferred embodiments of the disclosure. In the exemplary embodiments, the components which are described for the embodiments each constitute individual features of the disclosure, to be considered independently of each other, and which also modify the disclosure independently of each other. Therefore, the disclosure shall also encompass other than the presented combinations of features. Moreover, the described embodiments can also be amplified with other of the already described features of the disclosure.

In the figures, the same reference numbers denote elements of identical function.

Figure 1:
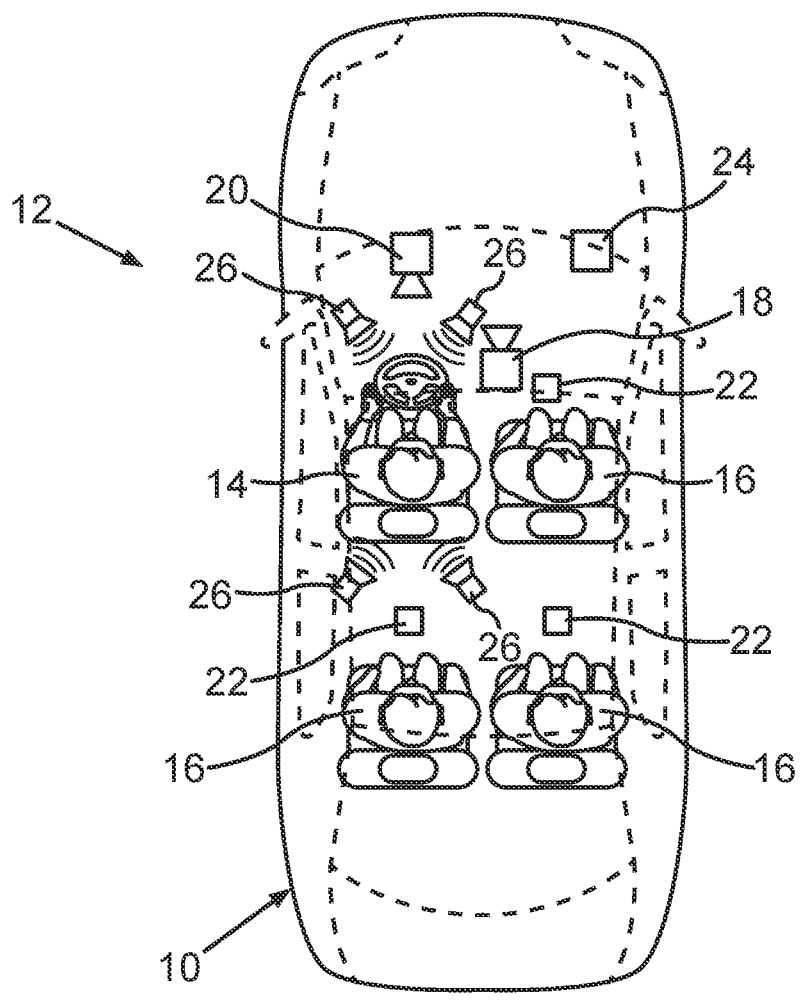
FIG. 1 shows a motor vehicle according to one exemplary embodiment.

FIG. 1 shows schematically a motor vehicle 10, in particular a schematic top view of the motor vehicle 10, having a system 12 for summarizing a conversation according to one exemplary embodiment. In the motor vehicle 10, which can be steered by a driver 14, several vehicle passengers 16 may be present, carrying on a conversation.

The system 12 may comprise a vehicle sensor device, and the vehicle sensor device may comprise vehicle exterior sensors, especially at least one vehicle exterior camera 18, and vehicle interior sensors, especially a vehicle interior camera 20, microphones 22, and/or a pulse sensor (not shown) for measuring the pulse rate of the driver 14. In order for the driver 14 not to be distracted by the conversation of the vehicle passengers 16 during a challenging driving task, yet still be able to take part in the conversation after the driving task, it is preferably provided that the conversation is masked for the driver 14 during the driving task and that he receives a summary afterwards of the conversation which was held.

For this, it can be ascertained by the vehicle sensor device, especially the vehicle exterior camera 18, whether a traffic situation is present in the surroundings of the motor vehicle 10 which corresponds to a given driving task criterion which implies a challenging driving task. For this, the vehicle exterior camera 18 can register other road users, a traffic infrastructure, such as a road condition and/or a traffic sign, and/or weather conditions, especially limited visibility, and provide these data to a computing device 24, on which an algorithm for artificial intelligence can be running. The algorithm for artificial intelligence is preferably adapted to evaluate the data of the vehicle sensor device and ascertain from these the presence or the imminence of the challenging driving task. Alternatively or in addition, the vehicle interior sensors, especially the vehicle interior camera 22, and/or pulse sensors can also be used to determine the challenging driving task, in order to determine a stress value of the driver 14, for example, by evaluating the behavior of the driver 14 by the computing device 24, especially by the algorithm for artificial intelligence, in which case the challenging driving task can be present if the stress value of the driver 14 is found to be above a stress threshold value. Navigation system data, especially the presence of a multiple-lane highway, a multiple-lane intersection, a freeway on ramp or off ramp, and/or increased traffic, also indicate the challenging driving task.

If such a challenging driving task is ascertained, the conversation being carried on in the motor vehicle 10 can be masked for the driver 14 in that the computing device 24 orders one or more loudspeakers 26 which can be arranged in suitable manner around the driver 14 to generate a counter noise which muffles the conversation by destructive interference for the driver 14. In other words, the counter noise creates a sound bubble around the driver 14, which screens out the conversation of the other vehicle passengers 16 from the driver 14.

Conversation contents or sound signals of the respective vehicle passengers 16 can be determined for the computing of the counter noise by one or more microphones 22, which are preferably present in the form of a microphone array and which measure the corresponding sound signal by way of a sound triangulation, in order to suitably actuate the loudspeakers 26 with the counter noise.

The microphones 22 can additionally be adapted to record the further conversation between the vehicle passengers 16 while the conversation is being masked for the driver 14. The recorded conversation can then be evaluated by the computing device 24, especially by an artificial intelligence or the artificial intelligence which is running on the computing device 24, where the evaluation involves a recognizing of conversation contents and/or conversation topics. These can then be summarized according to the most important statements made by the vehicle passengers 16.

Preferably, the summarizing can be broken down into different topic areas which were discussed. In order to make this summarizing more intuitive, it is possible to coordinate the conversation contents with user profile data, especially the name of the vehicle passenger 16, preferably with the aid of a respective user profile and a coordination with where or whom the respective conversation contents come from. For the coordination of the user profiles with the respective vehicle passengers 16, the respective vehicle passengers 16 can be determined with the aid of vehicle interior sensors, such as a voice recognition of the microphones 22, and/or a facial recognition by an or the vehicle interior camera 20, there being further possibilities for the recognizing of the vehicle passengers. The position from which a particular conversation content was enunciated can be determined preferably by the position of the microphones 22 or by a sound triangulation.

Especially preferably, a respective emotional state of the vehicle passengers 16 can also be determined during the recording of the conversation between the vehicle passengers 16, for example, by evaluating pictures of the vehicle interior camera 20 and/or by a voice analysis of the conversation contents recorded by the microphones 22. These can then be used by the artificial intelligence to annotate arguments together with a respective emotional state when pronouncing said arguments during the summarizing and to indicate, for example, whether an argument was only meant ironically or whether an argument produced a strong emotion in another vehicle passenger 16.

After the challenging driving task is over, which can likewise be recognized by the vehicle sensor device, the conversation as summarized by the artificial intelligence can be output for the driver 14, especially by the loudspeakers 26. In this process, the driver 14 can dictate, from the different topic areas of the conversation as recognized by the artificial intelligence, and preferably summarized according to a user preference, the topic areas for the output which are of interest to him. The topic areas corresponding to the user preference of the driver 14 may be predetermined and/or they may depend on the time of day and/or an emotional state of the driver 14. It can also be provided that the driver 14 can select the topic areas, for example, by a selection using a voice command or a touch control action.

After the summary of the conversation has been output, the counter noise can be deactivated, so that the conversation is again displayed to the driver 14 and he can again take part in it.

In addition, it can also be provided that each vehicle passenger 16 has a corresponding loudspeaker arrangement 26, which can mask the conversation separately for each individual vehicle passenger 16, and the masking can occur when a state of distraction of the vehicle passenger 16 corresponds to a given distraction criterion. The distraction criterion can be present, for example, when a vehicle passenger is making a telephone call and/or reading and does not wish to be distracted by the conversation. Accordingly, the conversation can be masked for the vehicle passenger 16 and a summarizing of the conversation can be produced by the artificial intelligence, which can be output to the vehicle passenger after the state of distraction is over.

Furthermore, depending on a user preference, a masking of the conversation can occur, for example, when certain conversation contents are of no interest to a vehicle passenger 16 and/or if a given conversation intensity, such as a dispute between other vehicle passengers, exceeds a user preference.

Figure 2:
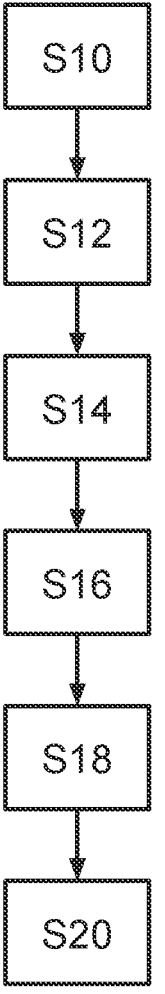
FIG. 2 shows a schematic diagram of a method according to one exemplary embodiment.

In FIG. 2, a schematic diagram of the method for summarizing a conversation in a motor vehicle 10 is represented according to one exemplary embodiment. In a step S10, a vehicle sensor device can determine whether a challenging driving task is present. For this, data from at least one vehicle exterior camera 18 and/or navigation system data can be checked by an artificial intelligence, running on a computing device 24 of the motor vehicle 10, for the presence of a given driving task criterion by which the challenging driving task can be ascertained. Alternatively or in addition, one or more vehicle interior sensors, especially a vehicle interior camera 20 which monitors the driver 14, can ascertain a stress value of the driver 14, from which the challenging driving task can be inferred. Especially preferably, a combined value can be determined from the data by the vehicle exterior sensor and the vehicle interior sensor, for example, by the artificial intelligence or by another artificial intelligence, and the challenging driving task can be present when this value is above a threshold value.

If such is the case, a conversation in the motor vehicle 10 can be masked for a driver position in step S12. Loudspeakers 26 and/or headphones of the driver 14 can be actuated to output counter noise which masks the conversation by way of destructive interference.

During the masking of the conversation, in step S14 the further conversation can be recorded by at least one vehicle microphone 22. The recorded conversation can be analyzed in step S16 by an artificial intelligence, preferably running on the computing device 24 of the motor vehicle 10, in order to coordinate conversation contents with the respective vehicle passengers and to sort the conversation by topic areas. For each of the topic areas, the recorded conversation can then be summarized, the conversation contents being preferably combined with the name of the particular person who enunciated the conversation contents, and especially preferably the emotion of the person during the conversation is additionally detected and included in the summarizing.

In step S18, after the challenging driving task is no longer present, the summarized conversation can be output for the driver, especially by one of the loudspeakers 26, and the driver will receive preferably only the topic areas corresponding to his user preference as the summary.

Finally, in step S20 the counter noise is deactivated after the output of the summarized conversation is finished.

In another exemplary embodiment, it is proposed that a conversation carried on by the passengers 16 in a motor vehicle 10 is automatically masked for the driver 14 in the presence of a challenging driving task during a trip with multiple passengers 16. By way of sensors installed in the motor vehicle 10, especially a vehicle exterior camera 18, a vehicle interior camera 20 observing at least the driver 14, microphones 22 and/or seat occupancy sensors, the current situation can be detected by one or more AI-algorithms which can be operated on a computing device 24.

Thanks to the use of the vehicle microphones 22, the vehicle interior camera 20 and the seat occupancy sensors, among other things, one or more AI algorithms can identify conversations, their content, and the persons participating in them. Challenging driving situations can be determined through the navigation database, especially multiple-lane intersections, off ramps, traffic jams or increased traffic, among other things. Thanks to the use of the exterior camera 18 and local weather data, poor visibility, especially rain or wind, can be identified. These serve as input quantities for the AI algorithm or another AI algorithm.

The condition of the vehicle passengers 16 can also be evaluated through the AI algorithm or another AI algorithm. The mental workload of the driver 14 can be determined by making use of the vehicle interior camera 20 and further sensors, such as pulse sensors.

Through loudspeakers 26 installed in the vehicle, the driver 14 can be deliberately bombarded with counter noise, especially by the loudspeakers 26 situated closest to him. The position and the microphones of the person 16 being masked can be used for the computing of the counter noise. The seat location of each speaking person can also be calculated especially preferably through microphone arrays and sound triangulation.

From the user profile which can be selected for each seat, the system 12 obtains information as to the identity of the persons present in the vehicle 10. This information helps in particular during a possible later summarizing of the recorded artefacts, so that these can be represented specifically for each position, especially in debates with strongly opposing positions. If the identify of a person cannot be determined, the algorithm can summarize their statement abstractly, for example, by indicating the location of the person in the motor vehicle 10.

A central unit (computing device 24) can determine when a situation demands that the driver 14 be supported automatically with the masking of the conversation and when to activate its masking, for example, by calculating a stress value. If the situation is resolved or the stress value falls below a defined stress threshold value, the conversation held in the meantime can be summarized by an AI algorithm, such as GPT-3, and read aloud to him. The masking is then ended and the driver 14 can again take part in the conversation.

The described method can preferably also be used in other application instances. Thus, during video or telephone conferencing, while a distraction of one of the conversation participants occurs, for example, during a further conversation, an audio signal of the video or telephone conferencing can preferably be masked for this participant. The conversation held in the meantime can then be summarized preferably by the artificial intelligence and be output to the conversation participant before rejoining the video or telephone conferencing.

Especially preferably, portions of the overall telephone call can also be evaluated and summarized and these can then be played back, for example, by a user input.

On the whole, the examples show how an AI-supported summarizing of a conversation can be provided by the disclosure.

German patent application no. 102022125547.6, filed Oct. 4, 2022, to which this application claims priority, is hereby incorporated herein by reference, in its entirety.

Aspects of the various embodiments described above can be combined to provide further embodiments. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A method for summarizing a conversation in a motor vehicle, the method comprising:
determining by a vehicle sensor device whether a challenging driving task is present;
if the challenging driving task is present, generating a counter noise that masks a conversation amongst occupants of the motor vehicle from a driver of the motor vehicle;
recording the conversation in the motor vehicle by at least one vehicle microphone and obtaining a recorded conversation while the counter noise is generated;
summarizing the recorded conversation by artificial intelligence while the counter noise is generated;
outputting a summary of the recorded conversation to the driver after determining that the challenging driving task is no longer present while the counter noise is generated;
deactivating the counter noise after the outputting the summary of the recorded conversation.

2. The method according to claim 1, wherein the determining whether the challenging driving task is present includes examining data from at least one vehicle exterior camera or navigation system by artificial intelligence for presence of a given driving task criterion.

3. The method according to claim 1, wherein the determining whether the challenging driving task is present includes determining a stress value of the driver by one or more vehicle interior sensors, the challenging driving task being present if the stress value is above a stress threshold value.

4. The method according to claim 1, further comprising:
determining respective positions in the motor vehicle from which conversation contents are coming by one or more vehicle interior sensors, wherein the summarizing of the conversation includes coordinating respective conversation contents of vehicle passengers with the respective positions in the motor vehicle, and calculating the counter noise based on the respective positions in the motor vehicle.

5. The method according to claim 4, further comprising:
determining whether a user profile is present for examining each vehicle passenger of the vehicle passengers by examining each vehicle passenger using one or more vehicle interior sensors, wherein the summarizing the conversation includes coordinating the conversation contents with user profile data of the user profile.

6. The method according to claim 1, further comprising:
determining an emotional state of a vehicle passenger during the conversation by one or more vehicle interior sensors, wherein the summarizing the conversation is based on the emotional state of the vehicle passenger.

7. The method according to claim 1, wherein the summarizing the conversation includes recognizing various topic areas of conversation and summarizing the various topic areas of conversation, and the outputting of the summary of the conversation is done only for one or more topic areas corresponding to a user preference.

8. The method according to claim 1, further comprising:
determining a state of distraction of a vehicle passenger,
masking the conversation for the vehicle passenger whose state of distraction corresponds to a given distraction criterion; and summarizing the conversation for the vehicle passenger whose state of distraction corresponds to the given distraction criterion.

9. The method according to claim 1, further comprising: masking the conversation for a vehicle passenger based on a user preference, given conversation contents, and conversation intensities.

10. A motor vehicle comprising:

one or more processors; and a memory storing one or more programs that, when executed by the one or more processors, cause the motor vehicle to:

determine by a vehicle sensor device whether a challenging driving task is present;

if the challenging driving task is present, generate a counter noise that masks a conversation amongst occupants of the motor vehicle from a driver of the motor vehicle;

record the conversation in the motor vehicle by at least one vehicle microphone and obtain a recorded conversation while the counter noise is generated;

summarize the recorded conversation as recorded by artificial intelligence while the counter noise is generated;

output a summary of the recorded conversation to the driver after the challenging driving task is determined to be no longer present while the counter noise is generated;

deactivate the counter noise after the summary of the recorded conversation is output.

11. The motor vehicle according to claim 10, further comprising:

at least one loudspeaker that, in operation, outputs the counter noise.

* * * * *